US008337470B2

(12) United States Patent
Prasad et al.

(10) Patent No.: US 8,337,470 B2
(45) Date of Patent: Dec. 25, 2012

(54) THREE-WAY VALVE FOR POWER INJECTION IN VASCULAR ACCESS DEVICES

(75) Inventors: Jayanthi Prasad, Clinton, MA (US); Tom Fisk, Natick, MA (US); Jeff Gray, Lexington, MA (US)

(73) Assignee: AngioDynamics, Inc., Latham, NY (US)

( * ) Notice: Subject to any disclaimer, the term of this patent is extended or adjusted under 35 U.S.C. 154(b) by 72 days.

(21) Appl. No.: 12/361,240

(22) Filed: Jan. 28, 2009

(65) Prior Publication Data

US 2010/0191192 A1    Jul. 29, 2010

(51) Int. Cl.
*A61M 5/00*    (2006.01)

(52) U.S. Cl. ............ 604/247; 604/27; 604/30; 604/246; 604/256; 604/537; 137/846; 137/854; 137/493.9; 137/512.4

(58) Field of Classification Search ............... 604/27, 604/30, 33, 43, 246, 247, 249, 256, 537; 137/846, 849, 493.1, 493.9, 854, 512.4, 512.5
See application file for complete search history.

(56) References Cited

U.S. PATENT DOCUMENTS

| | | | |
|---|---|---|---|
| 2,446,571 A | | 3/1944 | Browne |
| 2,720,881 A | | 10/1955 | Jones |
| 2,755,060 A | | 7/1956 | Twyman |
| 3,113,586 A | | 12/1963 | Edmark, Jr. |
| 3,159,176 A | * | 12/1964 | Russell et al. ............. 137/493.1 |
| 3,477,438 A | | 11/1969 | Allen et al. |
| 3,514,438 A | | 5/1970 | Nelsen et al. |
| 3,525,357 A | | 8/1970 | Koreski |
| 3,621,557 A | | 11/1971 | Cushman et al. |
| 3,669,323 A | | 6/1972 | Harker et al. |
| 3,673,612 A | | 7/1972 | Merrill et al. |
| 3,674,183 A | | 7/1972 | Venable et al. |
| 3,710,942 A | | 1/1973 | Rosenberg |
| 3,788,327 A | | 1/1974 | Donowitz et al. |
| 3,811,466 A | | 5/1974 | Ohringer |

(Continued)

FOREIGN PATENT DOCUMENTS

EP    0128625    12/1984

(Continued)

OTHER PUBLICATIONS

Asch, "Venous access: options, approaches and issues," Can Assoc. Radiol J., vol. 52, No. 3 pp. 153-164 (2001).

(Continued)

*Primary Examiner* — Bhisma Mehta
(74) *Attorney, Agent, or Firm* — Ryan D. Artis

(57) ABSTRACT

An apparatus for facilitating fluid flow between an internal body structure and a device external to the body comprises a housing having proximal and distal chambers separated from one another by a wall and fluidly connected to proximal port and distal ports. The wall includes a valve selectively sealing first and second openings thereof and a canopy biased toward a sealing position sealingly surrounding the first opening. The bias of the canopy is set to define a first pressure differential at which the canopy is moved out of the sealing position to permit fluid transfer therepast in a first direction. A duck-bill stem extends through the second opening and includes a lumen extending therethrough with walls of the stem being biased toward a sealing position and configured so that, when a second pressure differential is applied at at least a second level, the first end opens to permit flow therepast.

7 Claims, 7 Drawing Sheets

U.S. PATENT DOCUMENTS

| | | | |
|---|---|---|---|
| 3,941,149 A * | 3/1976 | Mittleman | 137/493.1 |
| 3,955,594 A | 5/1976 | Snow | |
| 4,072,146 A | 2/1978 | Howes | |
| 4,142,525 A | 3/1979 | Binard et al. | |
| 4,143,853 A | 3/1979 | Abramson | |
| 4,244,379 A | 1/1981 | Smith | |
| 4,387,879 A | 6/1983 | Tauschinski | |
| 4,405,316 A | 9/1983 | Mittleman | |
| 4,434,810 A | 3/1984 | Atkinson | |
| 4,447,237 A | 5/1984 | Frisch et al. | |
| 4,468,224 A | 8/1984 | Enzmann et al. | |
| 4,502,502 A | 3/1985 | Krug | |
| 4,524,805 A | 6/1985 | Hoffman | |
| 4,543,087 A | 9/1985 | Sommercorn et al. | |
| 4,552,553 A | 11/1985 | Schulte et al. | |
| 4,610,665 A | 9/1986 | Matsumoto et al. | |
| 4,616,768 A | 10/1986 | Flier | |
| 4,646,945 A | 3/1987 | Steiner et al. | |
| 4,673,393 A | 6/1987 | Suzuki et al. | |
| 4,681,572 A * | 7/1987 | Tokarz et al. | 604/329 |
| 4,692,146 A | 9/1987 | Hilger | |
| 4,722,725 A | 2/1988 | Sawyer et al. | |
| 4,790,832 A | 12/1988 | Lopez | |
| 4,798,594 A | 1/1989 | Hillstead | |
| 4,801,297 A | 1/1989 | Mueller | |
| 4,908,028 A | 3/1990 | Colon et al. | |
| 4,944,726 A | 7/1990 | Hilal et al. | |
| 4,946,448 A | 8/1990 | Richmond | |
| 4,960,412 A | 10/1990 | Fink | |
| 5,000,745 A | 3/1991 | Guest et al. | |
| 5,009,391 A | 4/1991 | Steigerwald | |
| 5,030,210 A | 7/1991 | Alchas et al. | |
| 5,084,015 A | 1/1992 | Moriuchi | |
| 5,098,405 A | 3/1992 | Peterson et al. | |
| 5,125,893 A | 6/1992 | Dryden | |
| 5,147,332 A | 9/1992 | Moorehead | |
| 5,149,327 A | 9/1992 | Oshiyama | |
| 5,167,638 A | 12/1992 | Felix et al. | |
| 5,169,393 A | 12/1992 | Moorehead et al. | |
| 5,176,652 A | 1/1993 | Littrell | |
| 5,176,662 A | 1/1993 | Bartholomew et al. | |
| 5,201,722 A | 4/1993 | Moorehead et al. | |
| 5,205,834 A | 4/1993 | Moorehead et al. | |
| 5,249,598 A | 10/1993 | Schmidt | |
| 5,254,086 A | 10/1993 | Palmer et al. | |
| 5,324,274 A | 6/1994 | Martin | |
| 5,330,424 A | 7/1994 | Palmer et al. | |
| 5,336,203 A | 8/1994 | Goldhardt et al. | |
| 5,360,407 A | 11/1994 | Leonard et al. | |
| 5,370,624 A | 12/1994 | Edwards et al. | |
| 5,395,352 A | 3/1995 | Penny | |
| 5,396,925 A | 3/1995 | Poli et al. | |
| 5,399,168 A | 3/1995 | Wadsworth et al. | |
| 5,401,255 A | 3/1995 | Sutherland et al. | |
| D357,735 S | 4/1995 | McPhee | |
| 5,405,340 A | 4/1995 | Fageol et al. | |
| 5,411,491 A | 5/1995 | Goldhardt et al. | |
| 5,453,097 A | 9/1995 | Paradis | |
| 5,454,784 A | 10/1995 | Atkinson et al. | |
| 5,469,805 A | 11/1995 | Gibbs | |
| 5,470,305 A | 11/1995 | Arnett et al. | |
| 5,484,420 A | 1/1996 | Russo | |
| 5,542,923 A | 8/1996 | Ensminger et al. | |
| 5,545,150 A | 8/1996 | Danks et al. | |
| 5,554,136 A | 9/1996 | Luther | |
| 5,562,618 A | 10/1996 | Cai et al. | |
| 5,571,093 A | 11/1996 | Cruz et al. | |
| 5,575,769 A | 11/1996 | Vaillancourt et al. | |
| 5,624,395 A | 4/1997 | Mikhail et al. | |
| 5,637,099 A | 6/1997 | Durdin et al. | |
| 5,667,500 A | 9/1997 | Palmer et al. | |
| 5,707,357 A | 1/1998 | Mikhail et al. | |
| 5,743,873 A | 4/1998 | Cai et al. | |
| 5,743,884 A | 4/1998 | Hasson et al. | |
| 5,743,894 A | 4/1998 | Swisher | |
| 5,752,938 A | 5/1998 | Flatland et al. | |
| 5,803,078 A | 9/1998 | Brauner | |
| 5,807,349 A | 9/1998 | Person et al. | |
| 5,810,789 A | 9/1998 | Powers et al. | |
| 5,843,044 A | 12/1998 | Moorehead | |
| 5,853,397 A | 12/1998 | Shemesh et al. | |
| 5,865,308 A | 2/1999 | Qin et al. | |
| 5,944,698 A | 8/1999 | Fischer et al. | |
| 5,984,902 A | 11/1999 | Moorehead | |
| 5,989,233 A | 11/1999 | Yoon | |
| 6,033,393 A | 3/2000 | Balbierz et al. | |
| 6,045,734 A | 4/2000 | Luther et al. | |
| 6,050,934 A | 4/2000 | Mikhail et al. | |
| 6,056,717 A | 5/2000 | Finch et al. | |
| 6,062,244 A | 5/2000 | Arkans | |
| 6,092,551 A | 7/2000 | Bennett | |
| 6,099,505 A | 8/2000 | Ryan et al. | |
| 6,120,483 A | 9/2000 | Davey et al. | |
| 6,152,909 A | 11/2000 | Bagaoisan et al. | |
| 6,210,366 B1 | 4/2001 | Sanfilippo | |
| 6,227,200 B1 | 5/2001 | Crump et al. | |
| 6,270,489 B1 | 8/2001 | Wise et al. | |
| 6,306,124 B1 | 10/2001 | Jones et al. | |
| 6,364,861 B1 | 4/2002 | Feith et al. | |
| 6,364,867 B2 | 4/2002 | Wise et al. | |
| 6,375,637 B1 | 4/2002 | Campbell et al. | |
| 6,436,077 B1 | 8/2002 | Davey et al. | |
| 6,442,415 B1 | 8/2002 | Bis et al. | |
| 6,446,671 B2 | 9/2002 | Armenia et al. | |
| 6,508,791 B1 | 1/2003 | Guerrero | |
| 6,551,270 B1 | 4/2003 | Bimbo et al. | |
| 6,610,031 B1 | 8/2003 | Chin | |
| 6,726,063 B2 | 4/2004 | Stull et al. | |
| 6,786,884 B1 | 9/2004 | DeCant et al. | |
| 6,874,999 B2 | 4/2005 | Dai et al. | |
| 6,953,450 B2 | 10/2005 | Baldwin et al. | |
| 6,994,314 B2 | 2/2006 | Garnier et al. | |
| 7,081,106 B1 | 7/2006 | Guo et al. | |
| 7,252,652 B2 | 8/2007 | Moorehead et al. | |
| 7,291,133 B1 | 11/2007 | Kindler et al. | |
| 7,316,655 B2 | 1/2008 | Garibotto et al. | |
| 7,435,236 B2 | 10/2008 | Weaver et al. | |
| 7,601,141 B2 | 10/2009 | Dikeman et al. | |
| 7,637,893 B2 | 12/2009 | Christensen et al. | |
| 7,758,541 B2 | 7/2010 | Wallace et al. | |
| 2001/0023333 A1 | 9/2001 | Wisse et al. | |
| 2001/0037079 A1 | 11/2001 | Burbank et al. | |
| 2002/0010425 A1 | 1/2002 | Guo et al. | |
| 2002/0016584 A1 | 2/2002 | Wise et al. | |
| 2002/0121530 A1 | 9/2002 | Socier | |
| 2002/0156430 A1 | 10/2002 | Haarala et al. | |
| 2002/0165492 A1 | 11/2002 | Davey et al. | |
| 2002/0193752 A1 | 12/2002 | Lynn | |
| 2003/0122095 A1 | 7/2003 | Wilson et al. | |
| 2004/0034324 A1 | 2/2004 | Seese et al. | |
| 2004/0064128 A1 | 4/2004 | Raijman et al. | |
| 2004/0102738 A1 | 5/2004 | Dikeman | |
| 2004/0108479 A1 | 6/2004 | Garnier et al. | |
| 2004/0186444 A1 | 9/2004 | Daly et al. | |
| 2004/0193119 A1 | 9/2004 | Canaud et al. | |
| 2004/0210194 A1 | 10/2004 | Bonnette et al. | |
| 2004/0267185 A1 | 12/2004 | Weaver et al. | |
| 2005/0010176 A1 | 1/2005 | Dikeman et al. | |
| 2005/0027261 A1 | 2/2005 | Weaver et al. | |
| 2005/0043703 A1 | 2/2005 | Nordgren | |
| 2005/0049555 A1 | 3/2005 | Moorehead et al. | |
| 2005/0149116 A1 | 7/2005 | Edwards et al. | |
| 2005/0171490 A1 | 8/2005 | Weaver et al. | |
| 2005/0171510 A1 | 8/2005 | DiCarlo et al. | |
| 2005/0283122 A1 | 12/2005 | Nordgren | |
| 2006/0129092 A1 | 6/2006 | Hanlon et al. | |
| 2006/0135949 A1 | 6/2006 | Rome et al. | |
| 2006/0149211 A1 * | 7/2006 | Simpson et al. | 604/403 |
| 2007/0161940 A1 | 7/2007 | Blanchard et al. | |
| 2007/0161970 A1 | 7/2007 | Spohn et al. | |
| 2007/0276313 A1 | 11/2007 | Moorehead et al. | |
| 2008/0108956 A1 | 5/2008 | Lynn et al. | |
| 2009/0292252 A1 | 11/2009 | Lareau et al. | |

FOREIGN PATENT DOCUMENTS

| | | |
|---|---|---|
| EP | 0337617 | 10/1989 |
| EP | 0864336 | 9/1998 |

| | | |
|---|---|---|
| EP | 0930082 | 7/1999 |
| EP | 1016431 | 7/2000 |
| FR | 2718969 | 10/1995 |
| GB | 966137 | 8/1964 |
| GB | 2102398 | 2/1983 |
| JP | 59133877 | 8/1984 |
| JP | 63255057 | 10/1988 |
| JP | 9038197 | 2/1997 |
| WO | WO-89/02764 | 4/1989 |
| WO | WO-91/12838 | 9/1991 |
| WO | WO-92/06732 | 4/1992 |
| WO | WO-95/16480 | 6/1995 |
| WO | WO-96/17190 | 6/1996 |
| WO | WO-96/23158 | 8/1996 |
| WO | WO-96/41649 | 12/1996 |
| WO | WO-97/23255 | 7/1997 |
| WO | WO-97/26931 | 7/1997 |
| WO | WO-98/22178 | 5/1998 |
| WO | WO-99/42166 | 8/1999 |
| WO | WO-00/06230 | 2/2000 |
| WO | WO-00/44419 | 8/2000 |
| WO | WO-01/74434 | 10/2001 |
| WO | WO-03/084832 | 10/2003 |
| WO | WO-2005/023355 | 3/2005 |
| WO | WO-2008/089985 | 7/2008 |

OTHER PUBLICATIONS

Herts et al., "Power injection of contrast media using central venous catheters: feasibility, safety, and efficacy," AJR Am. J. Roentgenol., vol. 176, No. 2, pp. 447-453 (2001).

Roth et al., "Influence of radiographic contrast media viscosity to flow through coronary angiographic catheters," Cathet. Cardiovasc. Diagn., vol. 22, No. 4, pp. 290-294 (1991).

Carlson et al., "Safety considerations in the power injection of contrast media via central venous catheters during computered tomogrphic examinations," Invest. Radiol., vol. 27, No. 5, p. 337-340 (1992).

Kaste et al., "Safe use of powr injectors with central and peripheral venous access devices for pediatrict CT," Pediatr. Radiol., vol. 26, No. 8, pp. 449-501 (1996).

Herts et al., "Power injection of intravenous contrast material through central venous catheters for CT: in vitro evaluation," Radiology, vol. 200, No. 3, pp. 731-735 (1996).

Rivitz et al., "Power injection of peripherally inserted central catheters," J. Vasc. Interv. Radiol., vol. 8, No. 5, pp. 857-863 (1997).

Rogalla et al., Safe and easy power injection of contrast material through a central line, Eur. Radiol., vol. 8, No. 1, pp. 148-149 (1998).

Williamson et al., "Assessing the adequacy of peripherally inserted central catheters for power injection of intravenous contrast agents for CT," J. Comput. Assist. Tomogr., vol. 25, No. 6, pp. 932-937 (2001).

Chahous et al., "Randomized comparison of coronary angiography using 4F catheters: 4F manual versus 'Acisted' power injection technique," Catheter Cardiovasc. Interv., vol. 53, No. 2, pp. 221-224 (2001).

Walsh et al., "Effect of contrast agent viscosity and injection flow velocity on bolus injection pressures for peripheral venous injection in first-pass myocardial perfusion studies," Technol. Health Care, vol. 10, No. 1, pp. 57-63 (2002).

Saito et al., "Diagnostic brachial coronary arteriography using a power-assisted injector and 4 French catheters with new shamps," J. Invasive Cardiol., vol. 9, No. 7, pp. 461-468 (1997).

International Search Report and Written Opinion mailed Mar. 17, 2010 for International Application No. PCT/US2010/021737 (8 pages).

International Preliminary Report on Patentability mailed Aug. 2, 2011 for International Application No. PCT/US2010/021737 (7 pages).

* cited by examiner

THREE-WAY VALVE FOR POWER INJECTION IN VASCULAR ACCESS DEVICES

BACKGROUND

The present invention relates generally to implantable valves for use with short or long term implantable vascular access devices. More specifically, the present invention relates to a system and method for employing pressure activated valves for use with, for example, peripherally inserted central catheters ("PICC"s). Conventional vascular access devices are surgically implanted under the skin to allow for repeated access to a selected vascular structure, such as an artery or a vein, for introducing fluids to and/or withdrawing fluids from the selected vascular structure.

SUMMARY OF THE INVENTION

The present invention is directed to an apparatus for facilitating fluid flow between an internal body structure and a device external to the body, the apparatus comprising a housing having proximal and distal chambers separated from one another by a wall and fluidly connected to proximal port and distal ports, respectively, the wall including first and second openings therethrough and a valve selectively sealing the first and second openings and including a canopy biased toward a sealing position sealingly surrounding the first opening, the bias of the canopy being set to define a first pressure differential at which the canopy is moved out of the sealing position to permit fluid transfer between the proximal and distal chambers in a first direction and a duck-bill stem extending through the second opening and including a lumen extending therethrough with walls of the stem surrounding a first end of the lumen being biased toward a sealing position in which the first end is closed, the bias of the walls of the stem surrounding the first end being set so that, when a second pressure differential applied between an exterior of the stem and the lumen is at least a second predetermined level, the first end opens to permit flow between the proximal and distal chambers.

DETAILED DESCRIPTION

Figure 1:
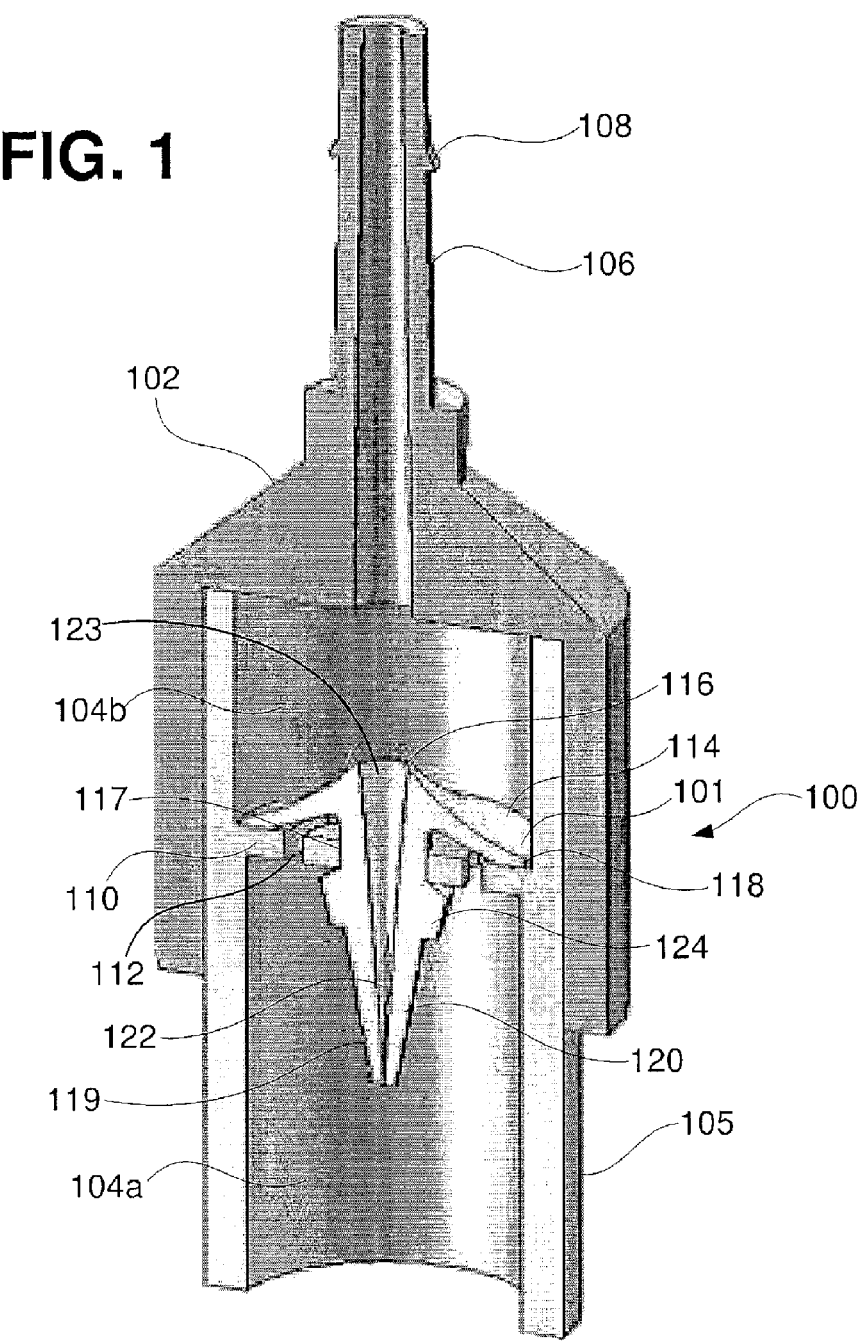
FIG. 1 shows a cross-sectional view of an exemplary three-way valve according to the present invention.

The present invention may be further understood with reference to the following description and the related appended drawings, wherein like elements are provided with the same reference numerals. The present invention describes an exemplary three-way valve for selective infusion and/or aspiration of fluids. Exemplary embodiments of the present invention may be employed for long-term (e.g., greater than 60 days) or short-term (e.g., less than 60 days) use in the body while the ability of the valve to seal after opening to permit fluid flow therethrough remains substantially constant over an extended period of time.

Figure 2A:
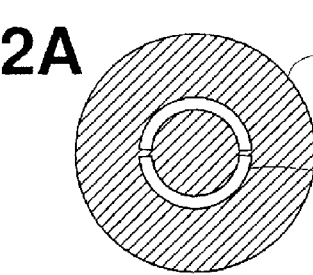
FIG. 2A shows one exemplary embodiment of a slotted opening for use in the valve of FIG. 1.
Figure 2B:
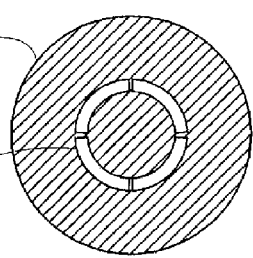
FIG. 2B shows a second exemplary embodiment of a slotted opening for use in the valve of FIG. 1.

As shown in FIGS. 1 and 2, a device 100 including a three-way valve 101 according to the present invention includes a housing 105 defining a first chamber 104a selectively fluidly connectable to a second chamber 104b and separated therefrom via the three-way valve 101. It is noted that the term proximal, as disclosed herein, refers to a direction approaching a user of the device while the term distal refers to a direction approaching a vascular structure being treated (i.e., into the body). Specifically, a substantially rigid wall 110 designed to retain its position and shape under the range of pressure differentials to which it is anticipated this device will be subjected separates the first chamber 104a from the second chamber 104b. The wall 110 may be formed of titanium or a rigid plastic such as, for example, Ultem. In an exemplary embodiment, the wall 110 may be a unitary element injection molded with the outer walls of the first and second chambers 104a and 104b, thereby ensuring a secure connection therebetween. The second chamber 104b is fluidly connected to a distal port 106 which is formed, for example, as a stem sized and shaped to receive the proximal end of a catheter or other suitable device known in the art to connect to a vascular structure (i.e., vein, artery, organ or other tissue mass in a living body) to deliver fluid thereto and/or to extract fluid therefrom, as those skilled in the art will understand. In an exemplary embodiment, radially abutting portions 108 are provided along the port 106 to aid in engaging the catheter or other device by, for example, enhancing a secure frictional engagement therewith. Although angularly formed radially abutting portions 108 are shown herein, it is noted that any of a number of other known securing means may be employed without deviating from the spirit and scope of the present invention. Furthermore, the port 106 may be formed to extend out of a body of the vascular access device 102 by varying lengths depending on the anatomy of an area of the body being treated. A proximal end of the vascular access device 102 further comprises a selectively permeably septum (not shown) when used in an implantable port (not shown), the septum being formed of a material to self-seal after penetration by a needle, as those skilled in the art will understand, for infusion and/or aspiration of fluids through the three-way valve 101 as will be described in more detail below. Furthermore, outer walls of the chamber 104a opposite and lateral to the septum (not shown) may be provided with a plate or other means known in the art to prevent a needle inserted therein from piercing the walls thereof, as those skilled in the art will understand.

A portion of the three-way valve 101 of the present invention is formed as an umbrella valve with a stem 119 extending proximally through the wall 110. A distal portion of the three-way valve 101 is umbrella-shaped with a canopy 114 extending proximally and radially outward from a distal-most end 116 thereof. The canopy 114 is biased toward a resting shape in which a peripheral portion 118 thereof sealingly contacts a distal surface of the wall 110. The three-way valve 101 of the present invention may be formed, for example, as a unitary element, of a single semi-rigid material shaped and sized to flex away from resting sealing positions to open positions only when acted upon by a predetermined threshold pressure differential as will be described in more detail below. The three-way valve 101 may be formed of a silicone material with deformable properties, the silicone being deformed under pressures ranging from approximately 0.2-300 psi. However, those skilled in the art will understand that the valve 101 may be composed of separate parts bonded (e.g., through welding, adhesives, etc.) of the same or different materials to obtain desired operating characteristics. A thickness of the canopy 114 may decrease from the end 116 of the valve 101 to the peripheral portion 118 thereof by an amount selected so that the increased flexibility of the peripheral portion 118 sets at a desired level the predetermined threshold differential at which the peripheral portion 118 will be flexed out of sealing contact with the distal surface of the wall 110. Alternatively, the canopy 114 may be formed with a uniform thickness with the thickness chosen in light of the material properties to achieve the desired threshold pressure. Furthermore, as would be understood by those skilled in the art, biasing members may be included in the material of the canopy 114 to achieve the desired operating characteristics of the valve 101.

The wall 110 includes one or more openings 112 radially within the peripheral portion 118 and sealed with respect to the chamber 104b thereby. The openings 112 may, for example, be formed as one or more arced slots distributed evenly about a centerline of the valve 101. The arc-shaped slots may be formed in any of a plurality of lengths and quantities and along any desired path, some of which are disclosed in FIGS. 2A and 2B. In an exemplary embodiment, the openings 112 formed as parts of a circle centered at a centerline of the valve 101 and separated from one another by parts of the wall 110 maintaining the structural integrity thereof. However, it is noted that many different configurations may be employed without deviating from the spirit and scope of the present invention. Accordingly, when the portion 118 is in the closed position, fluid in the chamber 104a is prevented from flowing into the chamber 104b and fluid in the chamber 104b is prevented from flowing past the valve 101 into the chamber 104a. Any material that does pass through the opening 112 remains trapped within the confines of the canopy 114.

When a user wishes to infuse a fluid into the body, a fluid delivery device is fluidly coupled to a proximal end of the device 100 (e.g., by attaching a syringe to a luer of a PICC or by inserting a needle through a self-sealing septum into the chamber 104a to supply fluid to the chamber 104a. When an infusion pressure in the first chamber 104a increases to the point at which the pressure differential applied by the fluid through the openings 112 against the proximal surface of the portion 118 reaches the predetermined threshold level, the portion 118 flexes distally out of contact with the wall 110 allowing fluid flow into the chamber 104b and out of the port 106 through a catheter or other conduit attached thereto to the target body structure. When the supply of fluid is terminated and the pressure differential applied to the proximal surface of the portion 118 drops below the threshold level, the portion 118 is flexed under its bias back to the sealing position engaging the wall 110 and preventing further fluid transfer between the chambers 104a and 104b.

The stem 119 of the valve 101 extends through a central opening 117 in the wall 110 proximally into the chamber 104a to a duck-bill opening 120 at a proximal end thereof. The stem 119 and the opening 120 allow aspiration of fluids from the target body structure into the chamber 104b and from there into the chamber 104a and out of the body as will be described in more detail below. Specifically, a distal portion of the stem 119 forms two parts separated by a slit with the two parts biased toward a sealing position in which the duck-bill opening 120 is sealed to prevent fluid transfer between the chamber 104b and the chamber 104a. The stem 119 includes a substantially conical lumen 122 extending therethrough from a distal opening 123 within the chamber 104b to the duck-bill opening 120 in the chamber 104a. A diameter of the lumen 122 decreases from the opening 123 to a minimum at the opening 120. In the sealing position, the distal parts of the stem 119 are in sealing contact with one another closing the duck-bill opening 120 and preventing fluid flow therethrough. Upon application of a negative pressure in the first chamber 104a (e.g., by applying a negative pressure to a syringe attached to the luer for a PICC or by withdrawing fluid therefrom via a needle inserted through a self-sealing septum (not shown)), the pressure differential between the chamber 104a and the lumen 122 moves the distal portions of the stem 119 away from one another opening the duck-bill opening 120 and permitting fluid flow through the lumen 122 from the chamber 104b to the chamber 104a and into the needle for withdrawal from the body. Then, when the negative pressure is no longer applied by the needle, the bias of the stem 119 urges the distal parts thereof back into sealing contact with one another preventing further fluid transfer between the chambers 104b and 104a.

Figure 3:
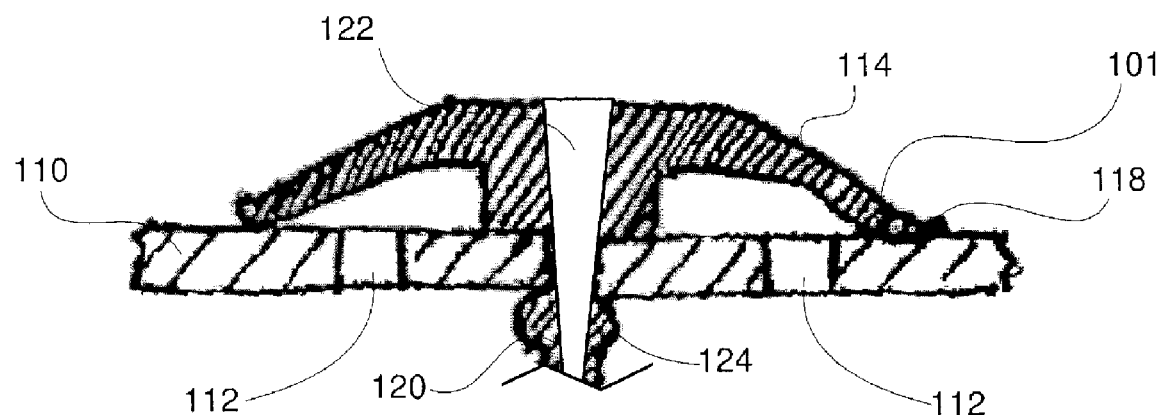
FIG. 3 shows a partial cross-sectional view of the three-way valve of FIG. 1.

The three-way valve 101 is further provided with at least one annular rib 124 engaging a portion of the wall 110 surrounding the hole 117 and preventing the valve 101 from being moved out of position within the hole 117 into either of the chambers 104a and 104b. Specifically, the annular rib 124 extends radially from the stem 119 to a diameter exceeding that of the hole 117 preventing distal movement of the valve 101 relative to the wall 110 while the canopy 114 extending radially outward from the distal portion of the stem 119 prevents movement of the valve 101 proximally through the hole 117 into the chamber 104a. As would be understood by those skilled in the art, the annular rib 124 may be formed in any of a plurality of configurations such as, for example, a trapezoidal configuration as shown in FIG. 1 (i.e., having a substantially trapezoidal cross-section in a plane including a longitudinal axis of the stem 119) and a rounded configuration as shown in FIG. 3. The annular rib 124, along with the substantially conical shape of the stem 119, also aids in directing fluids infused into the chamber 104a toward the openings 112 which are preferably adjacent to a radially outer edge of the annular rib 124.

Figure 4:
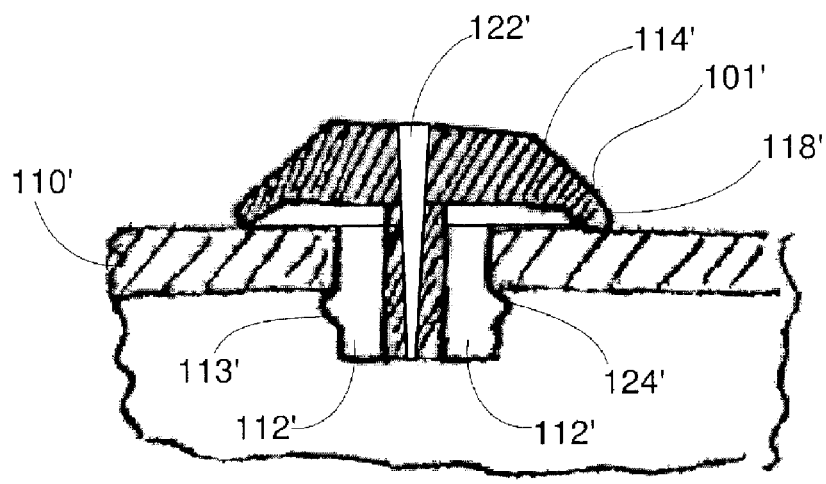
FIG. 4 shows a partial cross-sectional view of a three-way valve of FIG. 1.

FIG. 4 depicts an alternate embodiment of the valve of FIG. 3, wherein a valve 101' is shown with features substantially similar to those of the valve 101. Specifically, the valve 101' comprises a canopy 114' biased toward a resting shape in which a peripheral portion 118' thereof sealingly contacts a distal surface of a wall 110'. A substantially conical lumen 122' extends longitudinally therethrough to permit fluid flow from the chamber 104b to the chamber 104a and into a needle for withdrawal from the body. The wall 110' further comprises one or more openings 112' located radially within the peripheral portion 118' and sealed with respect to the chamber 104b thereby. The openings 112' are defined by a wall 113' extending proximally away from the wall 110' in order to further define a path of fluid flow therethrough. The wall 113' further comprises an annular rib 124' substantially adjacent to the wall 110'. The annular rib further defines an increased diameter portion of the opening 112', thus affecting a pressure and flow rate of fluid therethrough, as those skilled in the art would understand. Accordingly, the shape, size and location of the opening 112' may be chosen to affect a pressure and rate of flow to suit the requirements of a designated procedure, as those skilled in the art will understand.

Figure 5:
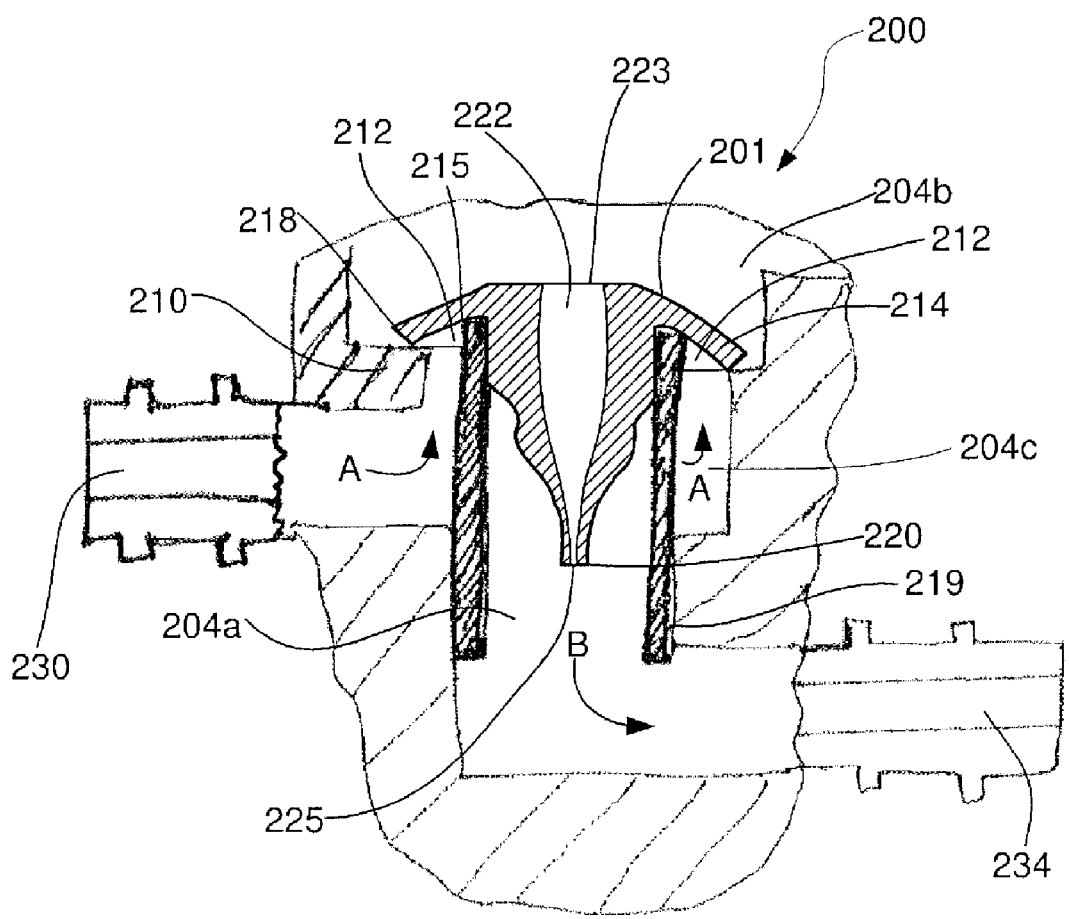
FIG. 5 shows a cross-sectional view of a three-way valve according to a second embodiment of the present invention.
Figure 6:
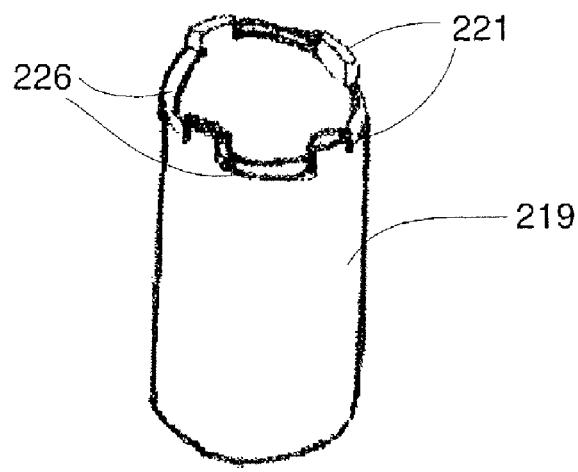
FIG. 6 shows a wall of an aspiration chamber of the device of FIG. 5.

As shown in FIGS. 5 and 6, a device 200 according to an alternate embodiment of the invention includes a three-way valve 201 functioning in a manner substantially similar to that of the valve 101 of FIG. 1 except as described below. The device 200 according to this embodiment includes separate infusion and aspiration ports 230, 234, respectively. The device includes a distal chamber 204b similar to the chamber 104b described above with an infusion chamber 204c open to the infusion port 230 and an aspiration chamber 204a open to the aspiration port 234. The chamber 204c extends from the port 230 to form an annular space surrounding the chamber 204a separated therefrom by a wall 219 and opening to a portion of the chamber 204b surrounded and sealed by a canopy 214 of the valve 201 via one or more openings 212 similar to the openings 112 described above. As with the canopy 114 described above, the canopy 214 is biased toward a resting shape in which a peripheral portion 218 thereof sealingly contacts a distal surface of a wall of the chamber 204b surrounding the openings 212. For example, the openings 212 may be formed as one or more arced slots distributed evenly about a centerline of the valve 201. The arc-shaped slots may be formed in any of a plurality of lengths and quantities and along any desired path or paths, for example, paths similar to those disclosed in FIGS. 2A and 2B. In an exemplary embodiment, the openings 212 are formed as parts of a circle centered at a centerline of the valve 201 and separated from one another by parts of a wall 210 maintaining the structural integrity thereof. The width of the chamber 204c may be selected to be less than a width of the canopy 214 of the valve 201 so that, when the canopy 214 is in the sealed position, flow is prevented between the chamber 204b and the chamber 204c. Alternatively, the chamber 204c maybe wider than the canopy 214 so long as radially outer edges of the openings 212 are radially within the outer edge of the canopy 214. As would be understood by those skilled in the art, the three-way valve 201 may be biased toward the sealed position by any of a number of known methods including, for example, insert molding, inclusion in the canopy 214 of separate biasing members, etc. Specifically, the three-way valve 201 may be loaded in position in an injection mold and plastic may then be injected therearound. Accordingly, the placement of the plastic will help to maintain a position of the three-way valve 201, even when subjected to a load by fluids injected or withdrawn therefrom. In an alternate embodiment, the three-way valve 201 may be held in place via one or more of a friction fit with the walls of the chamber 204b, welding, bonding, portions passed through openings in the walls 219 similar to the annular rib 124, etc.

FIG. 6 shows the wall 219 defining a distal portion of the chamber 204a and which extends into the chamber 204b. The wall 219 may be formed in an initial step and then inserted into a mold so that the rest of the device 200 may be injection molded therearound. The valve 201 may also be seated on the wall 219 prior to the injection molding. The wall 219 is formed with a plurality of indentations 221 defined by a plurality of recesses 226 disposed circumferentially along a distal end thereof. The indentations 221 aid in retaining the valve 201 in place in the housing 210 and prevent rotation thereof. Specifically, a portion of a proximal face 215 of the canopy 214 may be provided with respectively formed recesses (not shown) sized and shaped to interlockingly engage with the indentations 221.

The chamber 204a encircles the chamber 204b (e.g., as an annular space therearound). As described above, one or more openings 212 is formed at a distal end of the chamber 204a allowing fluids injected thereinto to flow against the proximal surface of the canopy 214 and, when a pressure differential between the chamber 204c and the chamber 204b exceeds a predetermined threshold level, the peripheral portion 218 of the canopy 214 is moved out of sealing engagement with the portion(s) of the wall of the chamber 204b surrounding the opening 212 into an open position permitting fluid flow from the chamber 204c into the chamber 204b in the direction of arrow A. The fluid then flows through the chamber 204b to a distal opening (not shown) into a conduit for delivery to the target body structure.

Aspiration from the target body structure via the three-way valve 201 is performed via the aspiration port 234 fluidly connected to the chamber 204b. Similar to the chamber 104a of FIG. 1, a stem 220 of a duck-bill portion of the valve 201 extends into the chamber 204a with a distal portion of the stem 220 sealing an opening at a distal end of the chamber 204a to the chamber 204b. The stem 220 includes a lumen 222 extending therethrough from a distal opening 223 in the chamber 204b to a proximal end 225 in the chamber 204a. A distal portion of the stem 220 forms two parts separated by a slit with the two parts biased toward a sealing position in which the proximal end 225 is sealed to prevent fluid transfer between the chamber 204b and the chamber 204a. The stem 220 includes a substantially conical lumen 222 extending therethrough from a distal opening 223 within the chamber 204b to an opening at the proximal end 225 in the chamber 204a. A diameter of the lumen 222 decreases from a maximum at the opening 223 to a minimum at the proximal end 225. In the sealing position, the distal parts of the stem 220 are in sealing contact with one another closing the duck-bill opening at the proximal end 225 and preventing fluid flow therethrough. Upon application of a negative pressure to the chamber 204a according to one of the methods disclosed earlier, the pressure differential between the chamber 204a and the lumen 222 moves the distal portions of the stem 220 away from one another opening the duck-bill opening at the proximal end 225 and permitting fluid flow through the lumen 222 from the chamber 204b to the chamber 204a in the direction of arrow B and into the needle for withdrawal from the body. Then, when the negative pressure is no longer applied by the needle, the bias of the stem 220 urges the distal parts thereof back into sealing contact with one another preventing further fluid transfer between the chambers 204b and 204a.

The device 200 of FIG. 5 may be used to perform infusion and aspiration procedures in succession without disconnecting either of the infusion and aspiration devices from the ports 230, 234. That is, infusion and aspiration devices may remain connected to the device 200 at the ports 230, 234, respectively, at the same time. These devices may then be activated or deactivated to change the operation from aspiration to infusion. In addition, the inclusion of separate infusion and aspiration chambers 204c, 204a, respectively, prevents fluids that remaining in the aspiration chamber 204a from being re-infused into the body.

Figure 7:
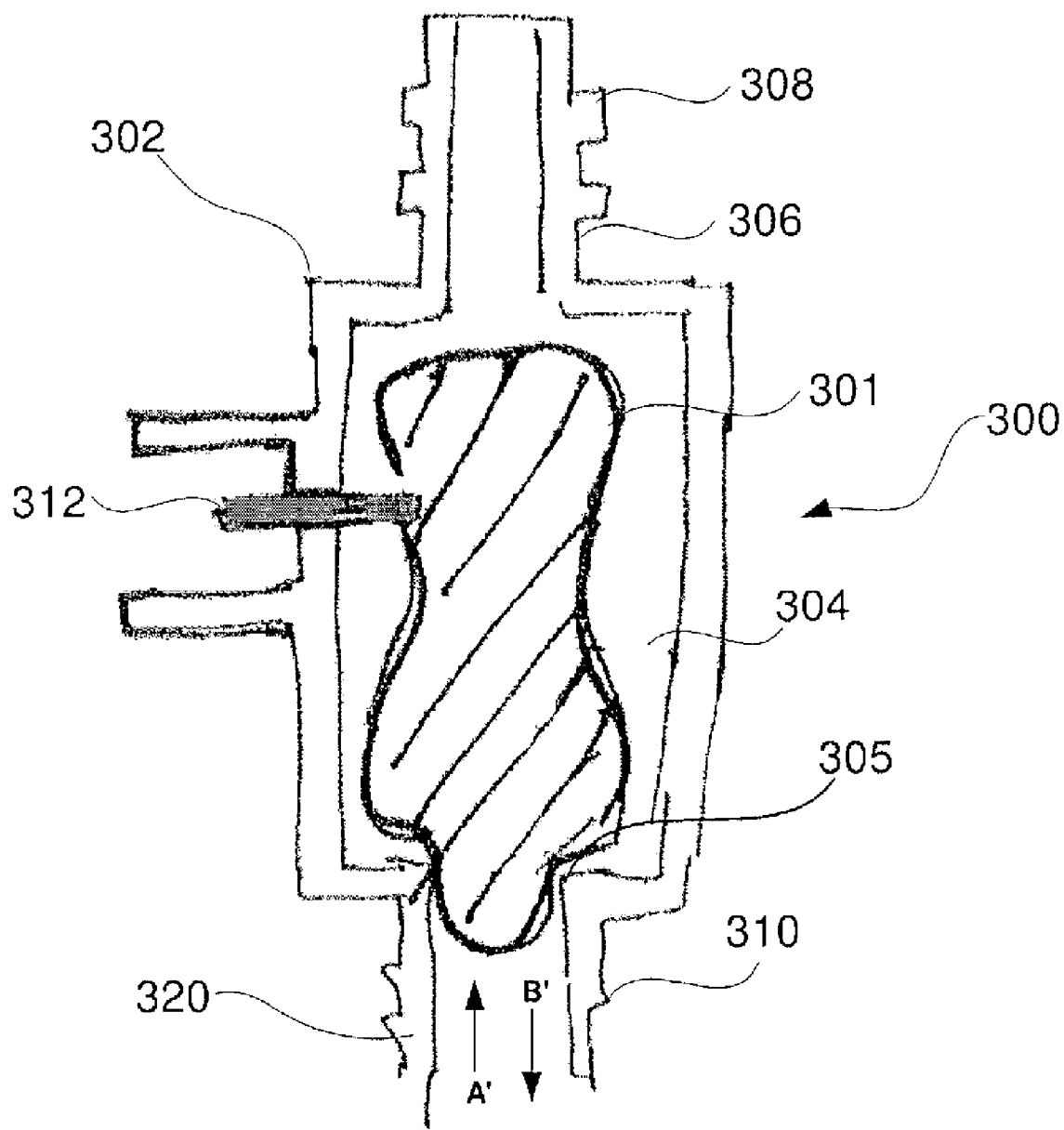
FIG. 7 shows a cross-sectional view of a three-way valve according to a third embodiment of the present invention.

In an alternate embodiment, as shown in FIG. 7, a device 300 includes a valve element 301 formed of an electroactive polymer ("EAP") which, as those skilled in the art will understand, deforms under the application of a voltage thereto. The valve element 301 is received within chamber 304 formed within a housing 302. The chamber 304 opens to a distal port 320 and a proximal port 306. The valve element 301, when in a sealing position, projects into and seals an opening 305 from the chamber 304 to the port 320 while, when in an open position, the valve element 301 is retracted from the opening 305 to permit flow therearound between the chamber 304 and the port 320. The valve element 301 is selectively coupleable (e.g., via a plug 312) to a source of electric energy to move the element 301 between the sealing and open positions. Thus, when it is desired to aspirate of infuse fluids to a target body structure (e.g., via a catheter or other conduit extending between the structure and the port 320), a user couples a source of the desired fluid pressure to the port 306 and applies the required electric energy to the element 301 via the plug 312 to move the element 301 into the open position. The applied voltage and current values may vary based on a selected geometry and size of material used for the device 300, as those skilled in the art will understand. This electric energy is supplied throughout the desired fluid transfer to maintain the element 301 in the open position. Then, when the desired fluid transfer has been completed, the supply of electric energy is suspended (e.g., by disconnecting the source from the plug 312) and the valve element 301 returns to the sealing position. As would be understood by those skilled in the art, the port 306 may include threading 308 or any other known connector to facilitate connection with the source of aspiration and/or infusion pressure while the port 320 may include barbed projections 310 or any other known connector to facilitate connection with a catheter or other conduit implanted to open to the target body structure.

Figure 8:
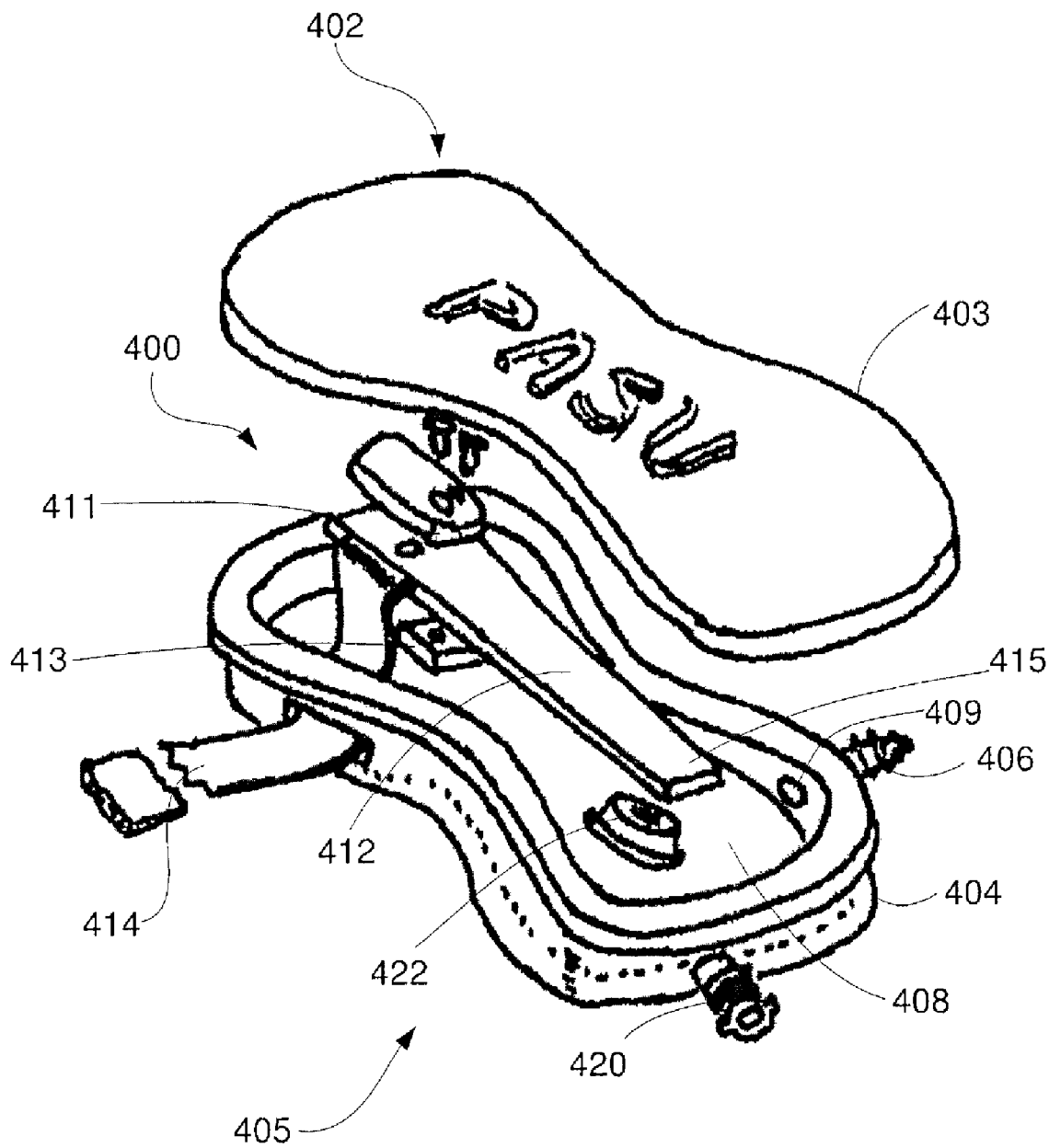
FIG. 8 shows an exploded view of a three-way valve according to a fourth embodiment of the present invention.

As shown in FIG. 8, a device 400 according to yet another embodiment of the invention includes housing 405 formed of, for example, a base member 404 and a cover 403 which mate to define a chamber 408. A distal port 420 extends through the base 404 to open to the chamber 408 via an opening 422 while a proximal port 406 passes through the base 404 to open into the chamber via an opening 409. A valve element formed as an arm 412 is mounted within the chamber 408 for movement between a sealing position in which the arm 412 covers the opening 422 and an open position in which the arm 412 is separated from the opening 422 to permit fluid flow between the distal port 420 and the chamber 408. The arm 412 may, for example, include a first end 411 adjacent to a piezoelectric element 413 while a second end 415 of the arm 412 extends over the opening 422. An electric lead 414 extends from the piezoelectric element 413 through the base 404 to provide a coupling for selectively energizing the piezoelectric element 413 as would be understood by those skilled in the art. As indicated in regard to the devices 100, 200 and 300 described above, the device 400 may be implanted under the skin and accessed for the infusion and/or aspiration of fluids to a target body structure via, for example, any known implanted port including a self-sealing septum or other access means, as also disclosed earlier. Such a port may be connected to the device 400 via a catheter or other conduit as would be understood by those skilled in the art.

As would be understood by those skilled in the art, the piezoelectric element 413 may comprise 2 or more piezoelectric sheets on either side of the arm 412 so that actuation of the element 413 causes a mechanical strain bending the cantilever arm 412 away from the opening 422. As would be understood by those skilled in the art, the lead 414 may extend through the skin to a port accessible to a user or to a known implanted inductive coupling. Alternatively, the lead 414 may extend to a PICC luer (not shown), wherein a proximal end thereof (not shown) is located externally to the body.

Accordingly, when infusion or aspiration of a fluid or other material is desired, an electrical potential is applied to the lead 414 activating the piezoelectric element 413 and causing the cantilever arm 412 to deflect away from the opening 422. At this point, fluid pressure (i.e., negative aspiration pressure or positive infusion pressure) applied to the port 406 (e.g., via a needle inserted into an implanted port fluidly connected thereto) causes fluid transfer between the catheter connected to the port 420 and the source of fluid pressure via the port 406. When the desired fluid transfer has been completed, the supply of electric energy is terminated and the cantilever arm 412 returns to the sealing position over the orifice 422 preventing further fluid transfer.

Figure 9A:
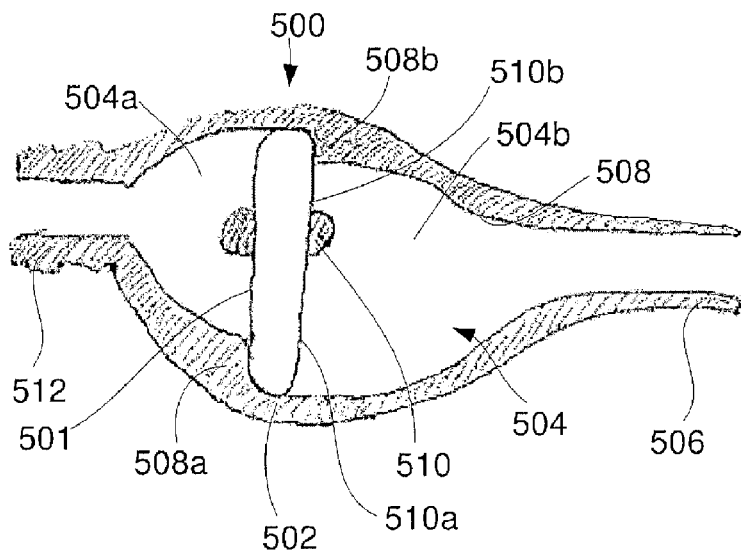
FIG. 9A shows a cross-sectional view of a three-way valve according to a fifth embodiment of the present invention in a closed state.
Figure 9B:
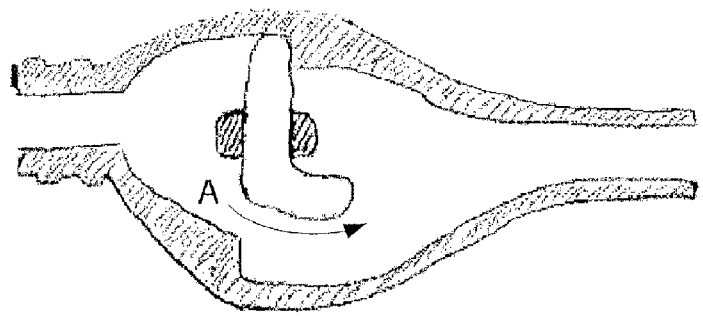
FIG. 9B shows a cross-sectional view of the three-way valve of FIG. 9A in a first open state.
Figure 9C:
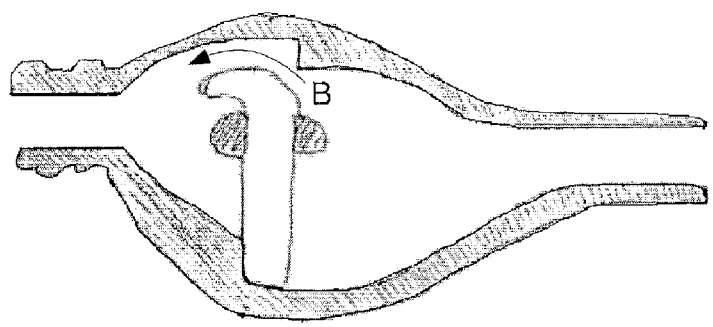
FIG. 9C shows a cross-sectional view of the three-way valve of FIG. 9A in a second open state.

As shown in FIGS. 9A-9C, a device 500 according to another embodiment of the invention, 9A-9C, includes a deflectable valve element 501 extending across a chamber 504 and dividing it into a proximal portion 504a and a distal portion 504b. An interior wall 508 of the housing 502 defining the chamber 504 includes first and second abutting walls 508a, 508b, respectively, abutting ends of the element 501. The first abutting wall 508a faces a proximal port 512 and the portion 504a of the chamber 504 while the second abutting wall 508b faces a distal port 506 and the portion 504b of the chamber 504. The valve element 501 is mounted to a base 510 extending into the chamber 504 and defining a first passage 510a between the portions 504a and 504b on a side of the base 510 adjacent the first abutting wall 508a and a second passage 510b between the portions 504a and 504b on a side of the base 510 adjacent the second abutting wall 508b. Although a central portion of the valve element 501 is rigidly coupled to the base 510 to prevent relative movement between the base and this central portion, the valve element 501 is flexible to permit the ends thereof to bend away from the first and second abutting walls 508a and 508b, respectively. In a sealing configuration, the valve element 501 extends across the chamber 504 and sealingly contacts both the first and second abutting walls 508a and 508b preventing all fluid flow between the portions 504a and 504b of the chamber 504. The valve element 501 remains in the sealing configuration at all times when a fluid pressure applied thereto is less than a predetermined threshold level (i.e., a level exceeding natural variations in pressure to which the device 500 would be exposed during normal activity of the patient and lower than the levels which would be applied in infusion and/or aspiration procedures).

As shown in FIG. 9B, when infusion pressure supplied to the port 512 exceeds the threshold level, the end of the element 501 in contact with the first abutting wall 508a is deflected distally out of sealing contact therewith and fluid flows through the passage 510a in the direction of arrow A from the portion 504a to the portion 504b and out of the port 506 to the target body structure as described above in regard to the previous embodiments. The other end of the valve element 501 is prevented from moving distally by the abutting wall 508b. When the infusion pressure drops below the threshold level, the valve element 501 returns to the sealing position in contact with the first abutting wall 508a and fluid flow is stopped.

As shown in FIG. 9C, when aspiration pressure supplied to the port 512 exceeds the threshold level, the end of the element 501 in contact with the second abutting wall 508b is deflected proximally out of sealing contact therewith and fluid flows through the passage 510b in the direction of arrow B from the portion 504b to the portion 504a and out of the port 512 for withdrawal from the body. The other end of the valve element 501 is prevented from moving proximally by the abutting wall 508a. When the aspiration pressure drops below the threshold level, the valve element 501 returns to the sealing position in contact with the second abutting wall 508b and fluid flow is stopped.

Figure 10A:
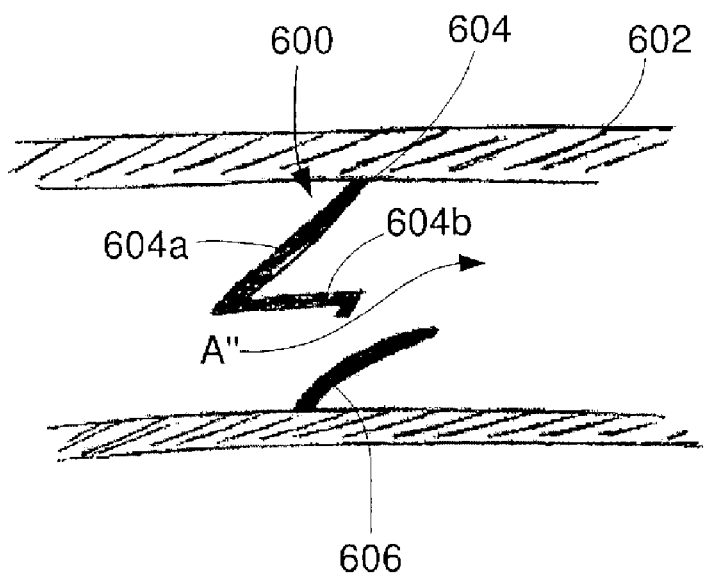
FIG. 10A shows a cross-sectional view of a three-way valve according to a sixth embodiment of the present invention in a first state.
Figure 10B:
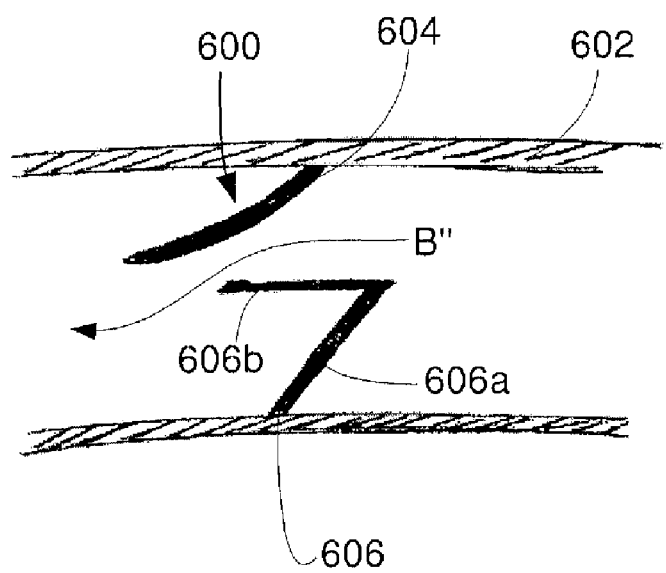
FIG. 10B shows a cross-sectional view of a three-way valve of FIG. 10A in a second state.

As shown in FIGS. 10A and 10B, a device according to a further embodiment of the invention includes a deflectable double reed valve element 600 within a housing 602. The double reed valve 600 may comprise, for example, two partial disk portions 604 and 606 extending laterally into a lumen of the housing 602. The disk portions 604 and 606 may be formed of a semi-rigid material designed to bend upon application of a minimum threshold pressure thereupon. In an exemplary embodiment, the valve 600 may be formed of stainless steel with a thickness of approximately 0.0254 mm or, alternatively, of a plastic material such as High Density Polyethylene, Polypropylene, etc. The stainless steel material may be cold rolled to achieve the desired thickness, as those skilled in the art will understand. If a plastic material is employed, an extrusion process may be used to form the valve, as disclosed in greater detail previously. Furthermore, proximal portions 604a and 606a, respectively, of each of the disk portions 604 and 606 may be formed of a more rigid material than distal portions 604b and 606b thereof. The proximal portions 604a and 606a may be mounted in the housing 602 in diagonal configurations, as shown in FIGS. 10A and 10B so that, in a sealing configuration, the distal portions 604b and 606b remain in sealing contact with one another preventing fluid flow through the lumen of the housing 602. Upon application of an infusion pressure of at least a threshold level, the distal portions 604b and 606b are deflected distally to permit infusion flow distally in the direction of the arrow A while the proximal portions 604a and 606a remain substantially in place. Upon application of an aspiration pressure of at least the threshold level, the distal portions 604b and 606b deflect proximally permitting aspiration flow proximally in the direction of arrow B while the proximal portions 604a and 606a remain substantially in place. It is further noted that, although the deflected portions in FIGS. 10A and 10B show pointed ends on the valve 600, the actual deflection may cause substantially rounded ends therein.

Those skilled in the art will understand that the embodiments described herein are for illustrative and descriptive purposes only and are not intended to limit the present invention which is to be limited only by the scope of the claims appended hereto. There are many modifications of the present invention which will be apparent to those skilled in the art without departing from the teaching of the present invention. For example, in any of the embodiments described herein, the directions of the components of the devices could be completely reversed with respect to the direction of flow (i.e., every instance of distal could be replaced with proximal or infusion replaced with aspiration) without departing from the scope of the invention. Furthermore, any of these devices may be implanted or external and may be employed to facilitate the transfer of any fluid with any body structure without departing from the scope of the invention. Furthermore, those skilled in the art will understand that for the valves disclosed herein that are activated by fluid pressure, the threshold level necessary to activate the valve for infusion may be set to the same or a different level than that set for aspiration. Still further, in any of the embodiments disclosed herein, the valves may be formed of a plurality of layers joined together. The multiple-layer valves may incorporate materials of differing properties to achieve deflection at predetermined threshold infusion and aspiration pressures.

What is claimed is:

1. An apparatus for flow control, comprising:
   a housing defining first and second chambers, wherein the second chamber is in fluid communication with a body lumen of a patient;
   a wall disposed between said first and second chambers, said wall defining a single central hole and a plurality of arc-shaped openings, said arc-shaped openings encircling the central hole; and
   a valve, comprising:
      a canopy disposed within said first chamber and configured to permit fluid flow through said arc-shaped openings from the second chamber to the first chamber when an infusion pressure in the first chamber reaches a predetermined threshold; and
      a duck-bill stem extending through the central hole and configured to permit fluid flow from the first chamber to the second chamber when a negative pressure is applied in the first chamber
      wherein the duck-bill stem has a substantially conical shape, and wherein each of an inner diameter, an outer diameter, and a wall thickness of said duck-bill stem decrease substantially linearly from a distal opening of the duck-bill stem to a proximal end of the duck-bill stem.

2. The apparatus of claim 1, wherein the first chamber is connectable to a syringe-for infusion into or withdrawal from a patient.

3. The apparatus of claim 1, wherein the central hole is characterized by a diameter and said valve includes at least one annular rib extending radially outward from the duck-bill stem, said at least one annular rib having a maximum outer diameter greater than the diameter of said hole.

4. The apparatus of claim 3, wherein said at least one annular rib engages with a portion of the wall defining said central hole to secure the valve therewithin.

5. The apparatus of claim 3, wherein said at least one annular rib has a outer surface shaped to direct fluid flow into and through said arc-shaped openings.

6. The apparatus of claim 1, wherein the canopy is characterized by a width, and the width of the canopy is sufficient to cover said arc-shaped openings.

7. The apparatus of claim 1, wherein each of the canopy and the duck-bill stem are biased towards a sealed position.

* * * * *